United States Patent [19]

Archibald et al.

[11] 4,447,604
[45] May 8, 1984

[54] THIAZOLOTRIAZINE DERIVATIVES

[75] Inventors: John L. Archibald, Farnham Royal; John T. A. Boyle, Cookham, both of England

[73] Assignee: John Wyeth & Brother Limited, Maidenhead, England

[21] Appl. No.: 364,561

[22] Filed: Apr. 1, 1982

[30] Foreign Application Priority Data

Apr. 10, 1981 [GB] United Kingdom ................. 8111371

[51] Int. Cl.³ .......................................... C07D 513/04
[52] U.S. Cl. ..................................................... 544/219
[58] Field of Search ........................................... 544/219

[56] References Cited

U.S. PATENT DOCUMENTS 4,127,660 11/1978 Boyle .................................. 544/219

OTHER PUBLICATIONS

Pratt and Ruddon, "The Anticancer Drugs", Oxford Univ. Press, New York (1979), pp. 273–276.
Carter et al. (Eds), "Principles of Cancer Treatment", McGraw-Hill Book Co., (1982), pp. 95, 107–114 & 121.

Primary Examiner—John M. Ford
Attorney, Agent, or Firm—Arthur G. Seifert

[57] ABSTRACT

Thiazolotriazine derivatives having the formula I

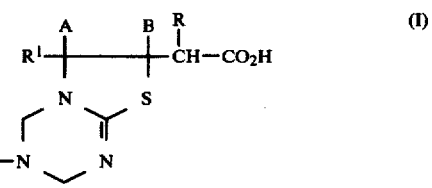

their pharmaceutically acceptable salts, pharmaceutically acceptable triazolotriazinium compounds containing the cation having formula II

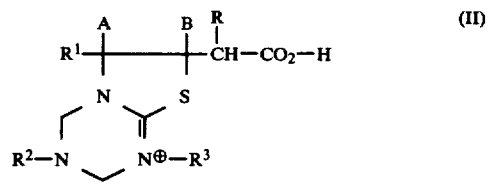

and their zwitterionic forms and pharmaceutically acceptable acid addition salts [where A is hydroxy whilst B is hydrogen or A and B together represent a direct bond; $R^1$ is aryl; $R^2$ and $R^3$ are independently lower alkyl or ar(lower)alkyl] are novel compounds useful as anti-cancer agents.

13 Claims, No Drawings

THIAZOLOTRIAZINE DERIVATIVES

The invention provides new thiazolotriazine derivatives and thiazolotriazinium compounds, a process for their preparation and pharmaceutical compositions containing them.

The new compounds provided by the invention are
(a) thiazolotriazine derivatives having the formula I

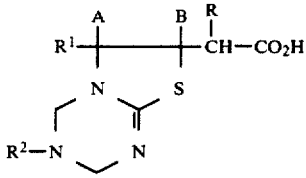

and their pharmaceutically acceptable salts and
(b) triazolotriazinium compounds comprising a cation having the formula II

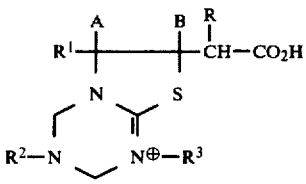

and a pharmaceutically acceptable anion and their zwitterionic forms and pharmaceutically acceptable acid addition salts.

In formulae I and II A represents —OH whilst B is hydrogen or A and B together represent a direct bond; R represents hydrogen or lower alkyl; $R^1$ represents aryl and $R^2$ represents ar(lower)alkyl or lower alkyl. In formula II $R^3$ represents ar(lower)alkyl or lower alkyl. The terms "aryl" and "ar", as in "ar(lower)alkyl", as used herein mean monovalent aromatic radicals. The aromatic radical may be carbocyclic or heterocyclic.

The compounds having formula I comprehend 3-[ar(-lower)alkyl or lower alkyl]-6-aryl-7-carboxyalkyl-6-hydroxy-3,4,6,7,-tetrahydro-2H-thiazolo[3,2-a]-s-triazines having the formula Ia

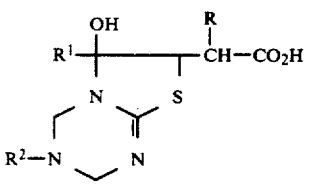

and 3-[ar(lower)alkyl or lower alkyl]-6-aryl-7-carboxyalkyl-3,4-dihydro-2H-thiazolo[3,2-a]-s-triazines having the formula Ib

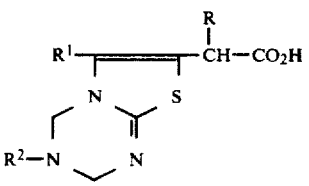

Similarly the cations having formula II comprehend 6-aryl-7-carboxyalkyl-1,3-di[ar(lower)alkyl or lower alkyl]-6-hydroxy-3,4,6,7-tetrahydro-2H-thiazolo[3,2-a]-s-triazinium ions having the formula

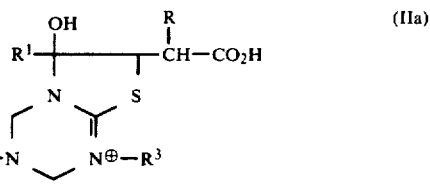

and 6-aryl-7-carboxyalkyl-1,3-di[ar(lower)alkyl or lower alkyl]-3,4-dihydro-2H-thiazolo[3,2-a]-s-triazinium ions having the formula IIb

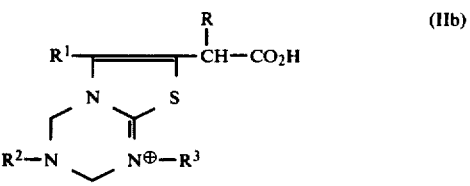

The symbol R represents hydrogen or lower alkyl, for instance methyl, ethyl, propyl or butyl. R preferably represents hydrogen or methyl. The aryl group denoted by $R^1$ may be, for example, unsubstituted phenyl or phenyl substituted by one or more substituents, preferably at most two substituents. As substituents for phenyl there may be mentioned halogen, for instance, chlorine or bromine; trifluoromethyl; lower alkoxy, for instance, methoxy, ethoxy, propoxy or butoxy; lower alkyl, for instance, methyl, ethyl, propyl or butyl; nitro; amino; substituted amino, for instance, mono- or di(lower alkyl) amino, for instance, methylamino, ethylamino, dimethylamino, methylethylamino or diethylamino; cyano; lower alkyl-sulphonyl, for instance, methylsulphonyl; lower alkyl-sulphinyl, for instance, methylsulphinyl; sulphamoyl and carbamoyl. $R^1$ preferably represents phenyl or phenyl substituted by an electron withdrawing group. $R^1$ may be, for instance, phenyl, halophenyl or nitrophenyl. $R^2$ and $R^3$, where present, are independently ar(lower)alkyl or lower alkyl, i.e. lower alkyl optionally monosubstituted by aryl. The lower alkyl may be, for instance, methyl, ethyl, propyl or butyl. The aryl group may be unsubstituted phenyl or phenyl substituted by one or more substituents, preferably at most two substituents. As substituents for phenyl there may be used those listed above under the meaning of $R^1$. $R^2$ and $R^3$, where present, are preferably methyl, ethyl, benzyl or phenylethyl.

The term "lower" as used herein in connection with alkyl and alkoxy groups means that the group contains up to 6 carbon atoms, preferably up to 4 carbon atoms.

It will be appreciated that the carbon atoms at the 6- and 7-positions in formulae I and II, that is the carbon atoms bearing the aryl group $R^1$ and the substituent —CHR—CO$_2$H, are asymmetric when A is —OH and B is hydrogen. Thus some of the compounds of the invention possess the property of stereoisomerism. The invention includes individual stereoisomers as well as their mixtures. Mixtures of stereoisomers may be separated in known manner.

Although the positive charge of the ion of formula II is shown on the nitrogen atom at the 1-position, it will be appreciated by those skilled in the art that the charge is believed to be delocalised between the 1-position and the 5-position. Thus the ion may equally well be illustrated by means of the formula IIc.

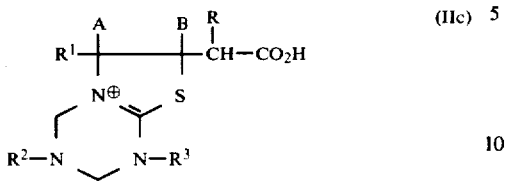

The pharmaceutically acceptable salts of the thiazolotriazine derivatives having formula I include those formed by salt formation at the carboxy group but are preferably acid addition salts. Such salts include these formed from inorganic acids, for instance, the sulphate, hydrochloride, hydrobromide, hydroiodide, nitrate, phosphate, and organic acids, for instance, the sulphonates (such as the methane-sulphonate and p-toluenesulphonate), acetate, maleate, fumarate, tartrate and formate. The acid addition salts may comprise the compound having formula I with one or two equivalents of acid.

The thiazolotriazinium salts containing $R^3$ may comprise the cation having formula II with a pharmaceutically acceptable anion. The anion may be derived from inorganic acids such as the chloride, bromide, ioidide, sulphate, nitrate, phosphate, and organic acids, for instance, sulphonates (such as the methanesulphonate and p-toluenesulphonate), acetate, maleate, fumarate, tartrate and formate. The invention further includes the pharmaceutically acceptable acid addition salts of the thiazolotriazinium compounds, in particular those salts comprising a cation which may be represented by the formula III

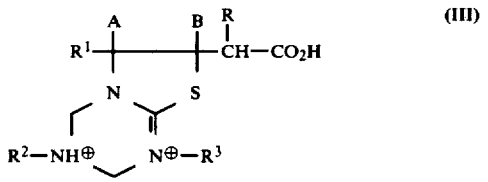

and a pharmaceutically acceptable anion, for instance, as described above. The invention also includes the zwitterionic forms of the thiazolotriazinium compounds and these may be represented by formula IV

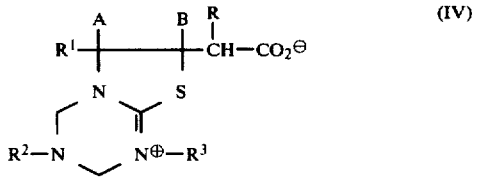

The compounds of the invention may be prepared by a process in which a compound having the formula

(wherein $R^1$ is as defined above, X represents $-CHR-CO_2H$ or a precursor therefor, R being as defined above, and Y represents a replaceable atom or group, for instance, a bromine atom or an organosulphonyloxy group, for example, p-toluenesulphonyloxy) is reacted with a triazine having the formula VI

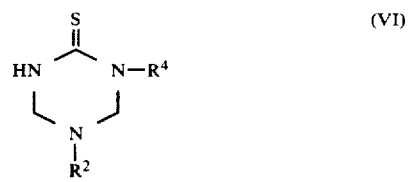

(where $R^2$ is as defined above and $R^4$ is hydrogen or the same as $R^3$). Where necessary, a precursor for $-CHR-CO_2H$ may be converted into $-CHR-CO_2H$ in known manner as a subsequent step. The process may also include conversion of one compound of the invention into another by treatment with a base or an acid.

The starting compounds having formula V are known or obtainable in known manner. The preferred starting materials are the α-bromo keto acids where X is $-CHR-CO_2H$ and Y is bromine. The α-bromo keto acids may be prepared by bromination of the corresponding keto acid, for instance, as described at J.Org.-Chem., 1945, 457 and J.Med.Chem., 17, 1180 (1974). The keto acids are generally known and may be prepared by the Friedel and Crafts reaction of aromatic compounds with succinic anhydride or a lower alkyl substitution product thereof, for instance, as described in Organic Reactions, 5, 229-289 (1949) published by John Wiley & Sons, Inc., or by other reactions, for instance, nitration. For example, the preparation of 3-(3-nitrobenzoyl)propionic acid by the nitration of 3-benzoylpropionic acid is described at J.Am.Chem. Soc., 58, 1441 (1936). The triazine derivatives of formula VI are known in some cases and, in the other cases, may be prepared in known manner. Two literature references relating to the preparation of the triazine derivatives are J.Am.Chem.Soc., 69, 2136 (1947) and British Pat. No. 775,823.

The reaction of the compound having formula V with the compound having formula VI can be carried out in solution in a suitable organic solvent, for instance, methanol. The choice of solvent is not critical provided that it is inert. The nature of the product obtained generally depends upon the temperature. Lower temperatures such as room temperature generally favour formation of the compounds where A is —OH whilst B is hydrogen. The use of higher temperatures favours the formation of the compound where A and B together form a direct bond. The most appropriate temperature to use in any particular case may be determined experimentally. A compound where A is hydroxy whilst B is hydrogen may be converted into one where A and B are a direct bond by heating in a solvent.

The product of the reaction of the compound having formula V with the compound having formula VI is generally a compound having the formula VIIa or VIIb

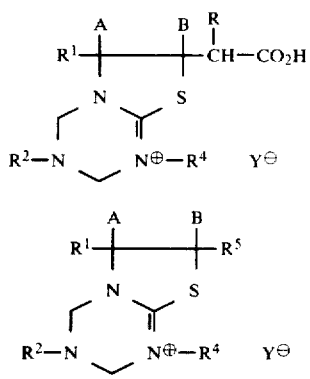

where in formula VIIb $R^5$ is a precursor for —CHR—CO$_2$H. We prefer to carry out the reaction so that the product is of formula VIIa. Where the product is of formula VIIb, the precursor should be capable of being converted to —CHR—CO$_2$H under such conditions that the thiazolotriazine ring structure survives. As an example of the precursor there may be mentioned the t-butyl ester group having the formula —CHR—CO—OC(CH$_3$)$_3$. The t-butyl ester may be cleaved to form the acid group under mild acidic conditions, for instance, in cool trifluoroacetic acid.

Once a compound according to the invention has been prepared it may be converted into another form of the same compound by treatment with a base or an acid. For instance treatment of a compound having formula VIIa where $R^4$ is the same as $R^3$ with a mild base, for instance, aqueous alkali metal carbonate or bicarbonate, may yield the zwitterionic form of formula IV. Treatment of a compound having formula VIIa where $R^4$ is hydrogen with a mild base, for example, aqueous alkali metal carbonate or bicarbonate yields a compound of formula I or, where excess base is used, a corresponding carboxylate salt. Addition of an acid to a compound having formula VIIa gives an acid addition salt.

The novel compounds of the invention are useful pharmaceutically, in particular as anti-cancer agents. Compounds are examined in the standard screening procedure of the National Cancer Institute, Bethesda, Md., USA, to determine activity against P388 lymphocytic leukemia in mice. The results presented below for test on female mice in the above procedure give the ratio of the median survival time of the treated mice (T) to the median survival time of the controls (C).

| Compound | Dose (mg/kg i.p.) | T/C |
|---|---|---|
| Example 1 | 200 | 141% |
| | 100 | 121% |
| Example 2(b) | 200 | 149% |
| | 100 | 125% |
| Example 3 | 200 | 121% |
| Example 4 | 100 | 126% |
| Example 5 | 100 | 300% |
| | 50 | 183% |
| | 25 | 160% |
| | 12.5 | 150% |
| Example 6 | 200 | 134% |
| | 100 | 134% |

The invention also provides a pharmaceutical composition comprising a novel compound of the invention in association with a pharmaceutically acceptable carrier. Any suitable carrier known in the art can be used to prepare the pharmaceutical composition. In such a composition, the carrier is generally a solid or liquid, or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups and elixirs. The active ingredient, for example, can be dissolved or suspended in a pharmaceutically acceptable liquid carrier such as water, an organic, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmoregulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilised by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in a unit dose of composition may be varied or adjusted from 0.5 mg to 750 mg, according to the particular need and the activity of the active ingredient. The invention also includes the compounds in the absence of the carrier where the compounds are in unit dosage form.

The following Examples illustrate the invention.

EXAMPLE 1

7-Carboxymethyl-6-hydroxy-3-methyl-6-phenyl-3,4,6,7-tetrahydro-2H-thiazolo[3,2-a]-s-triazine A solution of 3-benzoyl-3-bromo-propionic acid (6.4 g, 0.025 moles) in methanol (30 ml) was mixed with a solution of 5-methyl-3,4,5,6-tetrahydro-s-triazine-2(1H)-thione (3.27 g, 0.025 moles) in the same solvent (100 ml) and left for 3 hours. Evaporation of the solvent gave 7-carboxymethyl-6-hydroxy-3-methyl-6-phenyl-3,4,6,7-tetrahydro-2H-thiazolo[3,2-a]-s-triazine hydrobromide quarter hydrate as a pale yellow solid (8.8 g), m.p. 74°–77° C.

Analysis: Found: C, 42.7; H, 4.90; N, 10.8%. $C_{14}H_{17}N_3O_3S.HBr.\frac{1}{4}H_2O$ requires C, 42.8; H, 4.75; N, 10.7%.

EXAMPLE 2

7-Carboxymethyl-6-(p-chlorophenyl)-6-hydroxy-3-methyl-3,4,6,7-tetrahydro-2H-thiazolo[3,2-a]-s-triazine (a) A solution of 3-bromo-3-(p-chlorobenzoyl) propionic acid (7.29 g, 0.025 moles) in methanol (40 ml) was mixed with a solution of 5-methyl-3,4,5,6-tetrahydro-s-triazin-2(1H)-thione (3.27 g, 0.025 moles) in the same solvent (150 ml) and left for one hour. Evaporation of the solvent gave 7-carboxymethyl-6-(p-chlorophenyl)-6-hydroxy-3-methyl-3,4,6,7-tetrahydro-2H-thiazolo[3,2-a]-s-triazine hydrobromide as a pale yellow solid (9.6 g), m.p. 111°–113° C.

Analysis: Found: C, 39.6; H, 4.44; N, 9.85%. $C_{14}H_{16}ClN_3O_3S.HBr$ requires C, 39.8; H, 4.05; N, 9.94%.

(b) 7-Carboxymethyl-6-(p-chlorophenyl)-6-hydroxy-3-methyl-3,4,6,7-tetrahydro-2H-thiazolo[3,2-a]-s-triazine hydrobromide (2 g) was redissolved in the minimum quantity of methanol and immediately recrystallised to give 7-carboxymethyl-6-(p-chlorophenyl)-6-hydroxy-3-methyl-3,4,6,7-tetrahydro-2H-thiazolo[3,2-a]-s-triazine hydrobromide methanolate as colourless crystals (2.0 g), m.p. 138° C.

Analysis: Found: C, 39.4; H, 4.70; N, 9.54%. $C_{14}H_{16}ClN_3O_3S.HBr.CH_3OH$ requires C, 39.6; H, 4.65; N, 9.24%.

EXAMPLE 3

3-Benzyl-7-carboxymethyl-6-hydroxy-6-phenyl-3,4,6,7-tetrahydro-2H-thiazolo[3,2-a]-s-triazine 3-Benzoyl-3-bromopropionic acid (6.4 g, 0.025 moles) was dissolved in methanol (50 ml) and 5-benzyl-3,4,5,6-tetrahydro-s-triazine-2(1H)thione was partly dissolved in warm methanol and the solutions were mixed. The mixture was heated to reflux until a clear solution was obtained and this was allowed to stand for two hours at room temperature and was then evaporated to give a pale yellow foam (9.9 g, 84%). Two grams of this material were dissolved in methanol and diethyl ether added gradually until the cloudiness produced just disappeared. On standing, a colourless solid crystallised which was collected to give 3-benzyl-7-carboxymethyl-6-hydroxy-6-phenyl-3,4,6,7-tetrahydro-2H-thiazolo[3,2-a]-s-triazine hydrobromide three quarters hydrate (1.3 g), m.p. 124°–125° C.

Analysis: Found: C, 50.1; H, 4.76; N, 8.91%. $C_{20}H_{21}N_3O_3S.HBr.\frac{3}{4}H_2O$ requires C, 50.3; H, 4.96; N, 8.79%.

EXAMPLE 4

7-Carboxymethyl-6-hydroxy-3-methyl-6-(m-nitrophenyl)-3,4,6,7-tetrahydro-2H-thiazolo[3,2-a]-s-triazine A solution of 3-bromo-3-(m-nitrobenzoyl)propionic acid (7.55 g, 0.024 mole) in methanol (50 ml) was mixed with a solution of 5-methyl-3,4,5,6-tetrahydro-s-triazine-2(1H)thione (3.27 g, 0.025 mole) in the same solvent (170 ml). After 3 hours at room temperature the solvent was evaporated to small volume when a colourless solid crystallised, which was collected to give 7-carboxymethyl-6-hydroxy-3-methyl-6-(m-nitrophenyl)-3,4,6,7-tetrahydro-2H-thiazolo[3,2-a]-s-triazine hydrobromide methanolate (7.5 g), m.p. 144°–145° C. (decomposition).

Analysis: Found: C, 39.0; H, 4.54; N, 12.3%. $C_{14}H_{16}N_4O_5S.HBr.CH_3OH$ requires C, 38.7; H, 4.55; N, 12.0%.

EXAMPLE 5

3-Benzyl-7-carboxymethyl-6-hydroxy-6-(m-nitrophenyl)-3,4,6,7-tetrahydro-2H-thiazolo[3,2-a]-s-triazine A solution of 3-bromo-3-(m-nitrobenzoyl)propionic acid (3.78 g, 0.0125 mole) in methanol (50 ml) was mixed with a suspension of 5-benzyl-3,4,5,6-tetrahydro-s-triazin-2(1H)thione (2.6 g, 0.0125 mole) in the same solvent (150 ml). The mixture was warmed until a clear solution was obtained and allowed to stand for two hours. Evaporation of the solvent gave a yellow solid foam (5.3 g, 83%). 2.5 Grams of this material were dissolved in warm ethanol and a colourless solid gradually crystallised and was collected to give 3-benzyl-7-carboxymethyl-6-hydroxy-6-(m-nitrophenyl)-3,4,6,7-tetrahydro-2H-thiazolo[3,2-a]-s-triazine hydrobromide (1.2 g), m.p. 147°–148° C. (decomposition).

Analysis: Found: C, 47.5; H, 4.33; N, 10.9%. $C_{20}H_{20}N_4O_5S.HBr$ requires C, 47.2; H, 4.16; N, 11.0%.

EXAMPLE 6

3-Benzyl-7-carboxymethyl-3,4-dihydro-6-(m-nitrophenyl)-2H-thiazolo[3,2-a]-s-triazine 3-Bromo-3-(m-nitrobenzoyl)propionic acid (1.89 g, 0.00625 mole) and 5-benzyl-3,4,5,6-tetrahydro-s-triazin-2(1H)thione (1.3 g, 0.00625 mole) were stirred in ethanol (60 ml) at about 60° C. until all the triazinthione had dissolved (about 1 hour). After another hour a solid crystallised from the solution which was cooled and the solid collected to give the title compound as the hydrobromide ethanolate (0.65 g, 20%) m.p. 132°–134° (d).

Found: C, 48.7; H, 4.93; N, 10.5%. $C_{20}H_{18}N_4O_4S.HBr.C_2H_6O$ requires C, 49.2; H, 4.69; N, 10.4%.

EXAMPLE 7

7-Carboxymethyl-6-(p-chlorophenyl)-3,4-dihydro-3-(m-methoxybenzyl)-2H-thiazolo[3,2-a]-s-triazine 5-(m-Methoxybenzyl)-3,4,5,6-tetrahydro-s-triazin-2(1H) thione (2.37 g, 0.01 mole) was partly dissolved in methanol (100 ml) at 45° C. and 3-bromo-3-(p-chlorobenzoyl) propionic acid (2.92 g, 0.01 mole) dissolved in the same solvent (50 ml) was added. The temperature was held at about 45° C. until all the triazinthione dissolved, and the mixture was then allowed to stand for 3 hours. The solvent was evaporated to give a pale yellow foam, which was triturated with isopropanol to give the title compound hydrobromide hemipropanolate (2.4 g, 44%) m.p. 123°–125° C.

Found: C, 49.6; H, 4.86; N, 7.69%. $C_{21}H_{20}ClN_3O_3S \cdot HBr \cdot \frac{1}{2}C_3H_8O$ requires C, 50.0; H, 4.66; N, 7.77%.

EXAMPLE 8

7-Carboxymethyl-6-(p-chlorophenyl)-1,3-dimethyl-6-hydroxy-3,4,6,7-tetrahydro-2H-thiazolo[3,2-a]-5-triazinium bromide A solution of 3-bromo-3-(p-chlorobenzoyl) propionic acid (7.29 g, 0.025 moles) in methanol (40 ml) was mixed with a solution of 1,5-dimethyl-3,4,5,6-tetrahydro-s-triazin-2(1H)thione (3.625 g, 0.025 mole) in the same solvent (100 ml). After 2 hours at room temperature the solvent was evaporated to give a foam which was crystallised from isopropanol to give 7-carboxymethyl-6-(p-chlorophenyl)-1,3-dimethyl-6-hydroxy-3,4,6,7-tetrahydro-2H-thiazolo[3,2-a]-s-triazinium bromide as a colourless solid (6.0 g), m.p. 160°–161° C. (decomposition).

Analysis: Found: C, 41.8; H, 4.50; N, 9.54%. $C_{15}H_{19}BrClN_3O_3S$ requires C, 41.2; H, 4.38; N, 9.62%.

EXAMPLE 9

7-Carboxymethyl-1,3-dimethyl-6-hydroxy-6-phenyl-3,4,6,7-tetrahydro-2H-thiazolo[3,2-a]-5-triazinium bromide A solution of 3-benzoyl-3-bromo propionic acid (6.4 g, 0.025 moles) in methanol (40 ml) was mixed with a solution of 1,5-dimethyl-3,4,5,6-tetrahydro-s-triazin-2(1H)thione (3.625 g, 0.025 mole) in the same solvent (100 ml). After 2 hours at room temperature the solvent was evaporated to give a foam which was crystallised from isopropanol to give 7-carboxymethyl-1,3-dimethyl-6-hydroxy-6-phenyl-3,4,5,7-tetrahydro-2H-thiazolo[3,2-a]-s-triazinium bromide isopropanolate (10.05 g,), m.p. 154°–155° C. (decomposition).

EXAMPLE 10

A 3-bromo-X-propionic acid (where X is as given below) is reacted with an equimolar amount of a Y-3,4,5,6-tetrahydro-5-triazin-2(1H)thione (where Y is as given below) in a similar manner to Examples 1–5 to give a Z-3,4,6,7-tetrahydro-2H-thiazolo[3,2-a]-s-triazine hydrobromide (where Z is as given below)

| Meaning of X | Meaning of Y | Meaning of Z |
|---|---|---|
| 3-(m-aminobenzoyl) | 5-Benzyl | 6-(m-Aminophenyl)-3-benzyl-7-carboxymethyl-6-hydroxy |
| 3-(m-cyanobenzoyl) | 5-Ethyl | 7-Carboxymethyl-6-(m-cyanophenyl)-3-ethyl-6-hydroxy |
| 3-[p-dimethylamino)benzoyl] | 5-(m-Cyanobenzyl) | 7-Carboxymethyl-3-(m-cyanobenzyl)-6-(p-dimethylaminophenyl)-6-hydroxy |
| 3-(2',4'-dibromobenzoyl)-1-methyl | 5-(m-Nitrobenzyl) | 7-(1-Carboxyethyl-6-(2'4'-dibromophenyl)-6-hydroxy-3-(3'-nitrobenzyl) |
| 3-(m-trifluoromethylbenzoyl | 5-(m-Methylbenzyl) | 7-Carboxymethyl-6-hydroxy-3-(m-methylbenzyl)-6- |

-continued

| Meaning of X | Meaning of Y | Meaning of Z |
|---|---|---|
| 3-(p-methoxybenzoyl) | 5-[(p-Methylsulphonyl)benzyl] | (m-trifluoromethylphenyl) 7-Carboxymethyl-6-hydroxy-6-(p-methoxyphenyl)-3-[p-(methylsulphonyl)benzyl] |
| 3-(p-carbamoylbenzoyl) | 5-[p-(Dimethylamino)benzyl] | 6-(p-Carbamoylphenyl)-7-carboxymethyl-3-[p-(dimethylamino)benzyl]-6-hydroxy |
| 3-(p-sulphamoylbenzoyl) | 5-(p-Chlorobenzyl) | 7-Carboxymethyl-3-(p-chlorobenzyl)-6-hydroxy-6-(p-sulphamoylphenyl) |
| 5-[p-(methylsulphonyl)benzoyl] | 5-Methyl | 7-Carboxymethyl-6-hydroxy-3-methyl-6-[p-(methylsulphonyl)phenyl] |
| 5-(p-methylbenzoyl) | 5-(m-trifluoromethylbenzyl) | 7-Carboxymethyl-6-hydroxy-6-(p-methylphenyl)-3-(m-trifluoromethylbenzyl) |
| 5-[m-(methylamino)benzoyl] | 5-Methyl | 7-Carboxymethyl-6-hydroxy-3-methyl-6-[m-(methylamino)phenyl] |
| 5-[p-(methylsulphino)benzoyl] | 5-Benzyl | 3-Benzyl-7-carboxymethyl-6-hydroxy-6-[p-(methylsulphino)phenyl] |

We claim:
1. A compound selected from
(a) thiazolotriazine derivatives having the formula I

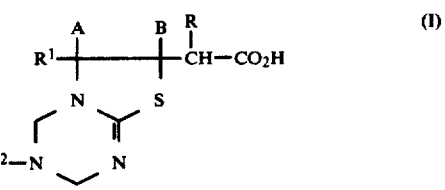

and their pharmaceutically acceptable salts and
(b) thiazolotriazinium compounds comprising a cation having the formula II

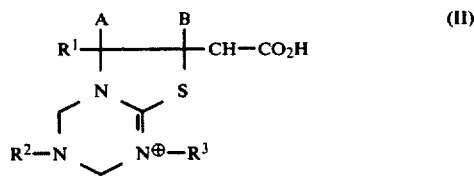

and a pharmaceutically acceptable anion and their zwitterionic forms and pharmaceutically acceptable acid addition salts; wherein
A is hydroxy whilst B is hydrogen or A and B together represent a direct bond;
$R^1$ represents aryl; $R^2$ is selected from lower alkyl and lower alkyl monosubstituted by aryl; $R^3$ (where present) is selected from lower alkyl and lower alkyl monosubstituted by aryl; and each aforesaid aryl is independently selected from unsubstituted phenyl and phenyl substituted by up to two substituents selected from halogen, trifluoromethyl, lower alkoxy, lower alkyl, nitro, amino, mono- and di-(lower alkyl) amino, cyano, lower alkylsulfonyl, lower alkylsulfinyl, sulfamoyl and carbamoyl.

2. A compound as claimed in claim 1, wherein R is selected from hydrogen and methyl.

3. A compound as claimed in claim 1, wherein $R^1$ is selected from phenyl, halophenyl and nitrophenyl.

4. A compound as claimed in claim 1, wherein $R^2$ and, if present, $R^3$ are independently selected from alkyl of 1 to 2 carbon atoms; benzyl, and benzyl substituted in the benzene ring by lower alkoxy.

5. A compound as claimed in claim 1, which is selected from 7-carboxymethyl-6-hydroxy-3-methyl-6-phenyl-3,4,6,7-tetrahydro-2H-thiazolo[3,2,-a]-s-triazine and the pharmaceutically acceptable acid addition salts thereof.

6. A compound as claimed in claim 1, which is selected from 7-carboxymethyl-6-(p-chlorophenyl)-6-hyroxy-3-methyl-3,4,6,7-tetrahydro-2H-thiazolo[3,2-a]-s-triazine and the pharmaceutically acceptable acid addition salts thereof.

7. A compound as claimed in claim 1, which is selected from 3-benzyl-7-carboxymethyl 6-hydroxy-6-phenyl-3,4,6,7-tetrahydro-2H-thiazolo[3,2-a]-s-triazine and the pharmaceutically acceptable acid addition salts thereof.

8. A compound as claimed in claim 1, which is selected from 7-carboxymethyl-6-hydroxy-3-methyl-6-(m-nitrophenyl)-3,4,6,7-tetrahydro-2H-thiazolo[3,2-a]-s-triazine and the pharmaceutically acceptable acid addition salts thereof.

9. A compound as claimed in claim 1, which is selected from 3-benzyl-7-carboxymethyl-6-hydroxy-6-(m-nitrophenyl)-3,4,6,7-tetrahydro-2H-thiazolo[3,2-a]-s-triazine and the pharmaceutically acceptable acid addition salts thereof.

10. A compound as claimed in claim 1, which is selected from 3-benzyl-7-carboxymethyl-3,4-dihydro-6-(m-nitrophenyl)-2H-thiazolo[3,2-a]-s-triazine and the pharmaceutically acceptable acid addition salts thereof.

11. A compound as claimed in claim 1 selected from 7-carboxymethyl-6-(p-chlorophenyl)-3,4-dihydro-3-(m-methoxybenzyl)-2H-thiazolo[3,2-a]-s-triazine and the pharmaceutically acceptable acid addition salts thereof.

12. A compound as claimed in claim 1, which is 7-carboxymethyl-6-(p-chlorophenyl)-1,3-dimethyl-6-hydroxy-3,4,6,7-tetrahydro-2H-thiazolo[3,2,-a]-s-triazinium bromide.

13. A compound as claimed in claim 1, which is 7-carboxymethyl-1,3-dimethyl-6-hydroxy-6-phenyl-3,4,6,7-tetrahydro-2H-thiazolo[3,2-a]-s-triazinium bromide.

* * * * *